United States Patent [19]

Wang et al.

[11] Patent Number: 5,334,785
[45] Date of Patent: Aug. 2, 1994

[54] PROCESS FOR THE MANUFACTURE OF 1,1,1,2-TETRAFLUOROETHANE

[75] Inventors: Li Wang, Bloomingdale; Timothy J. Barder, Addison; Mark Kaiser, Brookfield; Russell W. Johnson, Elmhurst; Blaise J. Arena, Des Plaines, all of Ill.

[73] Assignee: Allied-Signal Inc., Morris Township, Morris County, N.J.

[21] Appl. No.: 81,930

[22] Filed: Jun. 23, 1993

Related U.S. Application Data

[63] Continuation of Ser. No. 958,532, Oct. 8, 1992, abandoned, which is a continuation of Ser. No. 782,928, Oct. 25, 1991, abandoned.

[51] Int. Cl.$^5$ ............................................. C07C 17/08
[52] U.S. Cl. ................................... 570/165; 570/169
[58] Field of Search .......................... 570/168, 169, 165

[56] References Cited

U.S. PATENT DOCUMENTS

| | | | |
|---|---|---|---|
| 3,258,500 | 6/1966 | Swamer et al. | 260/653.7 |
| 3,395,187 | 7/1968 | Cristoph | 570/169 |
| 4,158,675 | 6/1979 | Potter | 570/169 |
| 4,766,260 | 8/1988 | Manzer et al. | 570/168 |
| 4,792,643 | 12/1988 | Soboley | 570/168 |
| 5,008,475 | 4/1991 | Manzer et al. | 570/168 |
| 5,155,082 | 10/1992 | Tung et al. | 502/228 |

FOREIGN PATENT DOCUMENTS

| | | |
|---|---|---|
| 701738 | 1/1965 | Canada ............................ 570/169 |
| 0408005 | 1/1991 | European Pat. Off. . |
| 0417680 | 3/1991 | European Pat. Off. . |
| 2252126 | 6/1975 | France . |
| 5027138 | 2/1980 | Japan . |

*Primary Examiner*—Alan Siegel
*Attorney, Agent, or Firm*—Harold N. Wells; Mary Jo Boldingh; Jay P. Friedenson

[57] ABSTRACT

An improved process for the vapor phase fluorination, especially fluorination of 1,1,1-trifluoro-2-chloroethane (CFC-133a) with HF to produce 1,1,1,2-tetrafluoroethane (HFC-134a) employs a catalyst which preferably consists essentially of boehmite and $Cr(OH)Cl_2 \cdot 2H_2O$, combined and extruded to form particulates and then heated in nitrogen.

7 Claims, 2 Drawing Sheets

PROCESS FOR THE MANUFACTURE OF 1,1,1,2-TETRAFLUOROETHANE

This application is a continuation of application Ser. No. 07/958,532 filed Oct. 8, 1992 now abandoned which is a continuation of Ser. No. 07/782,928 filed Oct. 25, 1991, now abandoned.

FIELD OF THE INVENTION

This invention relates generally to the fluorination of halogenated hydrocarbons. More specifically, it relates to the fluorination with MF of 1,1,1-trifluoro-2-chloroethane (CFC-133a) to produce 1,1,1,2-tetrafluoroethane (HFC-134a), a compound likely to replace CFC-12 (dichlorodifluoromethane) in certain applications.

PRIOR ART

CFC-12 is widely used in air conditioning equipment and other applications, but its use is being limited because of concern about depletion of the atmospheric ozone layer. One compound which may replace CFC-12 because it has much less potential for ozone depletion and has similar physical properties, is HFC-134a (1,1,1,2-tetrafluoroethane).

Many of the processes for preparing HFC-134a by reacting HF with CFC-133a employ catalysts entirely or partially composed of chromium oxides or fluorides.

In U.S. Pat. No. 3,258,500 fluorination with HF is carried out over an anhydrous chromium (III) oxide catalyst. In one aspect the catalyst is combined with alumina, although it is indicated that such supported catalysts are less effective.

In U.S. Pat. No. 4,158,675 a process is disclosed for producing HFC-134a by fluorination of CFC-133a using a basic chromium fluoride catalyst.

Two Japanese published applications, 55/027138 and 55/027139, also disclose vapor phase fluorination to produce HFC-134a using various Cr (III) compounds including chromium fluoride, oxides and oxyfluorides, which are pretreated under reaction conditions.

A catalyst prepared by co-depositing hexavalent chromium oxide and a transition metal compound on alumina and then fluorinating was suggested to be useful for the preparation of HFC-134a in U.S. Pat. No. 4,792,643.

In EP 331991A HFC-134a is produced using a metal catalyst, preferably cobalt, supported on $AlF_3$ or carbon.

Alumina is used as a support for a metal fluoride which may include chromium in WOS910341-A.

Chromium salts are impregnated on gamma-alumina in J02/157235A for a vapor phase reaction which produces CFC-123 rather than HFC-134a.

A supported chromium oxide or halide is used to make HFC-134a in J02/172933A.

Chromium is supported on $AlF_3$ for preparation of HFC-134a in U.S. Pat. Nos. 4,766,260 and 5,008,475.

The possibility that HFC-134a will become a volume commercial product has caused renewed interest in improved processes to prepare it. The present invention particularly relates to a catalyst for such an improved process. In addition, the catalyst of the invention has application to other related fluorinations.

SUMMARY OF THE INVENTION

Vapor phase fluorination of hydrocarbons and/or halogenated hydrocarbons, and in particular fluorination of 1,1,1-trifluoro-2-chloroethane (CFC--133a) to 1,1,1,2-tetrafluoroethane (HFC-134a), may be carried out at fluorination conditions in the presence of HF over a catalyst produced by mixing an acidic chromium compound, preferably a chromium hydroxy chloride, $Cr(OH)Cl_2.2H_2O$ with an aluminum oxide hydrate, preferably boehmite and water, then extruding pellets and heating in nitrogen (not air).

In one embodiment the catalyst is prepared by mixing 95 to 9 wt. % of a finely powdered boehmite (particles of about 10 to 75 microns) with 5 to 91 wt. % of $Cr(OH)Cl_2.2NH_2O$ and water to form a dough, which is then extruded to form particles suitable for use in a fixed bed reactor. The particles may be dried at a temperature of about 20° C. to 120° C. in air, preferably 70° C. to 100° C., and thereafter, heated in nitrogen at 300° C. to 650° C., preferably 400° C. to 550° C., and held at the maximum temperature for about 2 to 12 hours, preferably about 4 hours.

The process may be carried out in the vapor phase with a mole ratio of HF to CFC-133a of 10/1 to 1/1. Preferably, the mole ratio would be about 5/1 to 2/1. The reaction conditions include a temperature in the range of about 300° C. to 450° C., preferably a temperature of about 325° C. to 400° C., and a pressure in the range of 100 to 2,000 kPa, preferably about 172 to 517 kPa gauge. In a fixed bed reactor the liquid hourly space velocity will be about 0.5 to 5.0 $hr^{-1}$, preferably about 0.75 to 2 $hr^{-1}$, based on the feedstock.

BRIEF DESCRIPTION OF THE DRAWINGS

FIGS. 1 and 2 show the activity and selectivity of catalysts of the invention in converting CFC-133a to HFC-134a.

DESCRIPTION OF THE PREFERRED EMBODIMENTS

The Catalyst

Figure 1:
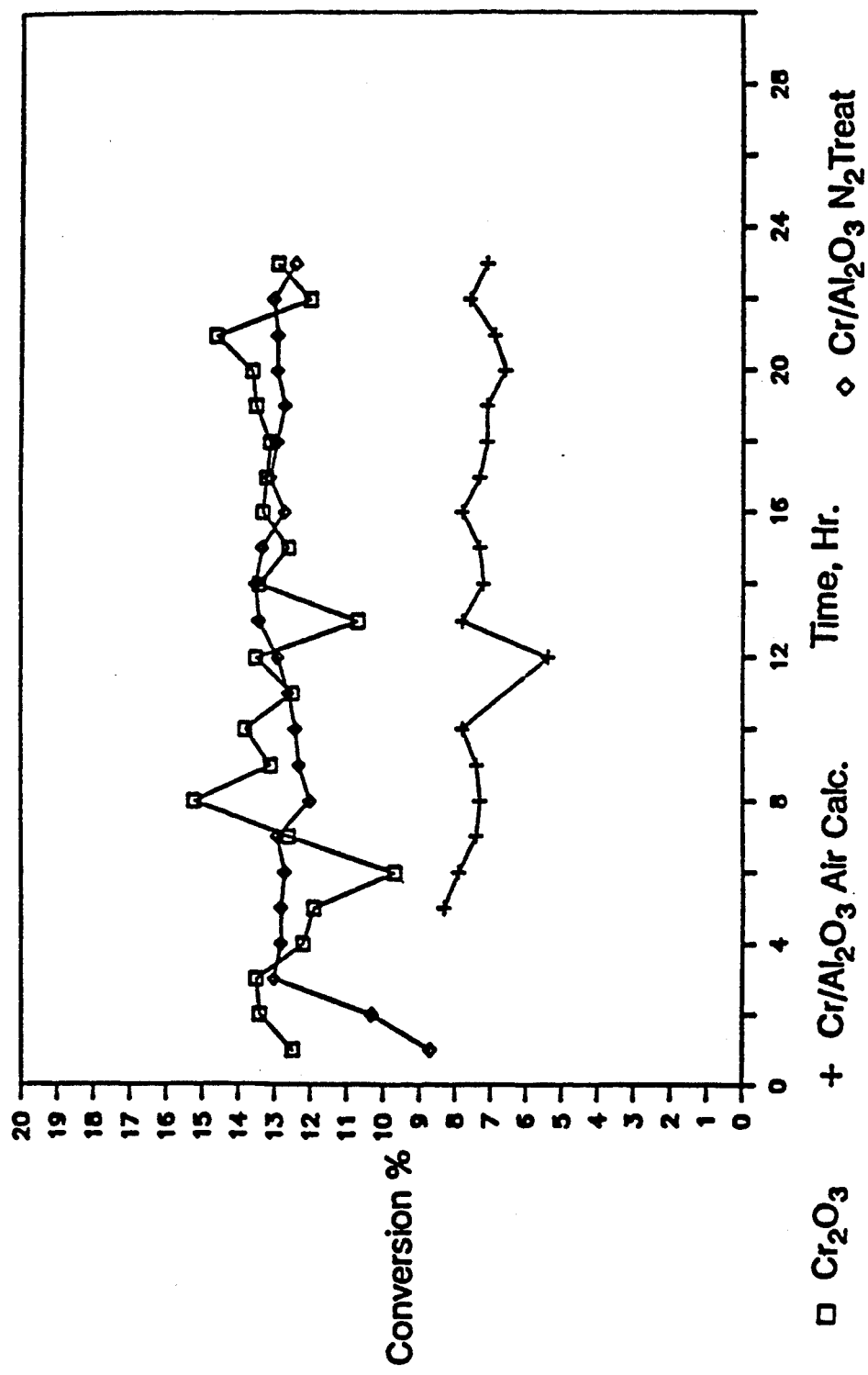

The catalyst is made from an aluminum oxide hydrate, preferably boehmite (alpha alumina monohydrate i.e., AlO(OH) or $Al_2L_3.H_2O$) and an acidic chromium compound, preferably $Cr(OH)Cl_2.2H_2O$ since the combination has been found to provide performance similar to the $CrF_3$ or $Cr_2O_3$ catalysts of the prior art, but at substantially lower cost. Preferably, the catalyst is the product resulting from calcining a mixture of about 95 to 9 wt. % boehmite and about 5 to 91 wt. % of $Cr(OH)Cl_2.2H_2O$. Preferably, the mixture will contain about 90 to 65 wt. % boehmite and about 35 to 10 wt. % of $Cr(OH)Cl_2.2H_2O$, along with sufficient water to bind the mixture.

Other aluminum oxide hydrates such as beta aluminum oxide monohydrate or alpha or beta alumina trihydrate may be substituted for boehmite, although not necessarily with equivalent results.

Other acid chromium compounds may be substituted for $Cr(OH)Cl_2.2H_2O$, such as $CrCl_3$, $Cr(NO_3)_3$, $Cr(OH)(CH_3COO)_2$, $Cr(CH_3COO)_3$, and $Cr_3(OH)_2(CH_3COO)_7$, although not necessarily with equivalent results. The acid chromium compounds are believed to peptize the aluminum oxide hydrate particles, resulting in a strong extrudate or pellet.

The catalyst precursor may be prepared by extrusion, pelletizing or other methods of compacting the mixture. Preferably, an extrudable dough is formed by mixing a finely divided boehmite powder, preferably about 10 to 75 microns in size, with $Cr(OH)Cl_2.2H_2O$ and water until a mixture suitable for extrusion results. Generally, such an extrudable dough must have suitable viscosity and stiffness. The dough may be extruded by various devices known in the art, such as an auger extruder or hydraulic piston extruder. This generally requires pressures in the range of 35 to 6894 kPa in order to form extrudates suitable for use in a fixed bed reactor. Such extruded particles typically will have a diameter in the range of about 1.5 to 2 mm and have a length of about 1 to 3 times the diameter. After being extruded the particles will be dried in air at temperatures in the range of about 20° C. to 120° C., preferably 80° C. to 100° C., and then heated in nitrogen (not air) at about 300° C. to 650° C., preferably 400° C. to 550° C., for a suitable period of about 2 to 12 hours, preferably about 4 hours. The calcining operation serves to convert boehmite to $\gamma$-$Al_2O_3$ and to convert $Cr(OH)Cl_2.2H_2O$ to surface amorphous $Cr_2O_3$. The calcined particles are then ready to be used in the fluorination of CFC-133a to HFC-134a. As will be seen below, heating the catalyst in nitrogen provides improved performance relative to heating the same catalyst in air.

Fluorination Process

Fluorination of hydrocarbons and partially halogenated hydrocarbons may be carried out using the catalyst of the invention. Hydrogen atoms or halogen atoms are replaced by fluorine atoms by reaction with HF. For example, when hydrogen fluoride is reacted with 1,1,1,-trifluoro-2-chloroethane (CFC-133a) its chlorine atom is replaced with a fluorine atom, yielding 1,1,1,2-tetrafluoroethane (HFC-134a). In addition to fluorination of CFC-133a, it is possible to fluorinate trichloroethylene to produce HFC-134a. Also, other halogenated hydrocarbons may be fluorinated with the catalyst of the invention, including such compounds as perchloroethylene ($CCl_2CCl_2$), partially chlorinated ethylenes, and chloro- and chlorofluoromethanes.

Although the reaction itself is generally known, the yield of HFC-134a is affected by the catalyst used and the reaction conditions. Generally, as will be seen, the reaction will be carried out with the catalyst of the invention at temperatures in the range of about 300° C. to 450° C., preferably about 325° C. to 400° C. and at pressures in the range of 100 to 2,000 kPa, preferably about 172 to 517 kPa (gauge). The mole ratio of HF/feed will be in the range of about 10/1 to 1/1, preferably 5/1 to 2/1. The liquid hourly space velocity for a fixed bed reactor will be about 0.5 to 5.0 $hr^{-1}$, preferably about 0.75 to 2 $hr^{-1}$, based on the feedstock. Using the catalyst of the invention, about 10 to 30% of the CFC-133a in the feed is typically converted with a selectivity to HFC-134a of about 90 to 99%.

It is desirable to pretreat the catalyst before introducing the feedstock, e.g. CFC-133a, by exposing the calcined catalyst to HF mixed with an inert gas (about 5 to 50 wt. %) at a temperature of about 325° C. to 400° C. for about 1 to 10 hours. Thereafter, feed can be introduced along with HF and some air (5 to 25 volume percent and the fluorination reaction initiated. The temperature will be adjusted to provide the desired conversion of the feed consistent with a high selectivity. Unreacted CFC-133a is recovered from the effluent by distillation and recycled to the reactor. The product HFC-134a is separated from the by-products by distillation and purified as required for the expected end use.

EXAMPLE 1

A sample of 200 g of boehmite having 27.2% volatiles supplied by Kaiser Aluminum & Chemical Co. was mixed with 54.6 g of $Cr(OH)Cl_2.2H_2O$ in a powder blender. 240 g of deionized water was added to the powder blend and mixing was continued to form a dough, which was dried by indirect heating with steam until an extrudable consistency was reached. The dough was extruded to form 1/12 inch (2.12 mm) cylindrical extrudates. These extrudates were reduced to an average length/diameter ratio of 3/1. They were then dried in an oven at 90° C. for 18 hours. After drying half of the extrudates were calcined in a muffle furnace at 500° C. for 4 hours, while the other half was heated in nitrogen (to 300° C. at 3° C./min and then to 500° C. at 1° C./min and held there for 4 hours).

EXAMPLE 2

Figure 2:
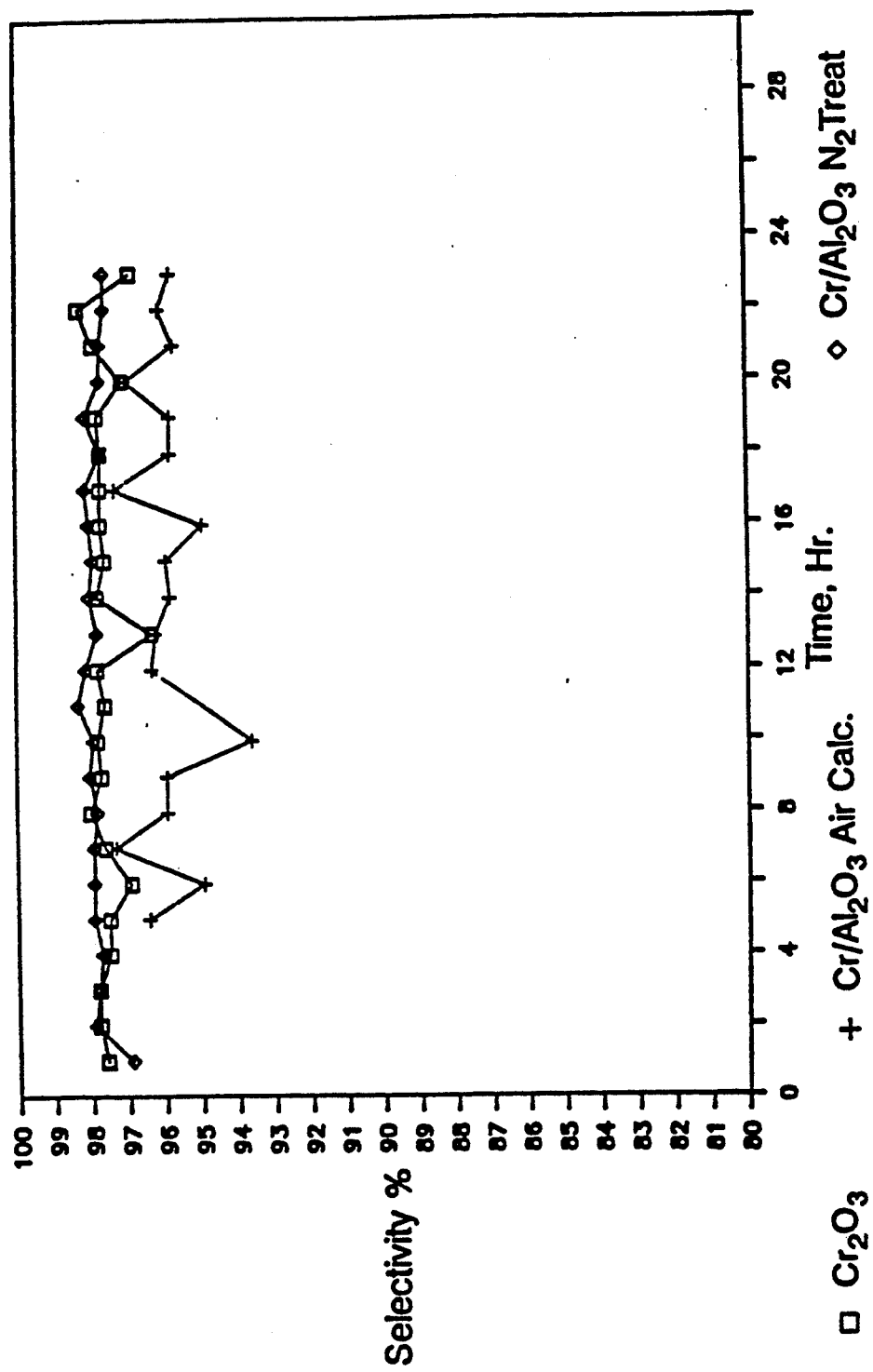

The catalyst prepared in Example 1 were tested by grinding the extrudates of Example 1 to 20–40 mesh size and then placing 30 mL of the particles in a 0.5 inch diameter i.d. (12.7 mm) reactor and then passing HF and CFC-133a (2.5/1 mol ratio) over the catalysts at a liquid hourly space velocity of 1.0 $hr^{-1}$ (based on CFC-133a) at a temperature of 350° C. and a pressure of 45 psig (310 kPa gauge). The results showed the superiority of the extrudates which had been heated in nitrogen, as will be seen in FIGS. 1 and 2. The performance of the catalyst of the invention was equivalent to that of prior art catalysts consisting solely of $Cr_2O_3$ and superior to the extrudate calcined in air instead of nitrogen with respect to both activity and selectivity. Since the catalyst of the invention is significantly less expensive than the conventional catalyst containing only chromium oxides, the catalyst of the invention provides an advantage to the user while retaining the performance of the conventional catalyst.

We claim:

1. A process for the vapor phase fluorination of hydrocarbons and or halogenated hydrocarbons with hydrogen fluoride over a catalyst at fluorination conditions wherein said catalyst consists essentially of the product of heating in nitrogen at a temperature of about 300° C. to 650° C. a mixture of an aluminum oxide hydrate selected from the group consisting of boehmite, beat aluminum oxide monohydrate, and alpha or beta alumina trihydrate and an acidic chromium compound selected from the group consisting of $Cr(OH)Cl_2.2H_2)$ $CrCl_3$, $Cr(NO_3)_3$, $Cr(OH)(CH_3COO)_2$, $Cr(CH_3COO)_3$ and $(Cr(OH)_2(CH_3COO)_7$, said chromium having a valence of 3.

2. The process of claim 1 wherein said catalyst is produced from a mixture of 95 to 9 wt. % boehmite and 5 to 91 wt. % of $Cr(OH)Cl_2.2H_2O$.

3. The process of claim 1 wherein said catalyst is produced from a mixture of 90 to 65 wt. % boehmite and 10 to 30 wt. % $Cr(OH)Cl_2.2H_2O$.

4. The process of claim 1 wherein 1,1,1-trifluoro-2-chloroethane (CFC-133a) is fluorinated to 1,1,1,2-tetrafluoroethane (HFC-134a).

5. The process of claim 4 wherein said process is carried out at temperatures within the range of 325° C. to 400° C. and pressures of about 100 to 2,000 kPa and with a mole ratio of hydrogen fluoride to 1,1,1-trifluoro-2-chloroethane of 10/1 to 1/1.

6. The process of claim 5 wherein the mole ratio of HF/CFC-133a is about 5/1 to 2/1.

7. The process of claim 5 wherein the catalyst is disposed as a fixed bed and the liquid hourly space velocity is about 0 5 to 5 0 $hr^{-1}$ based on feedstock.

* * * * *

UNITED STATES PATENT AND TRADEMARK OFFICE
CERTIFICATE OF CORRECTION

PATENT NO. : 5,334,785
DATED : Aug. 2, 1994
INVENTOR(S) : Li Wang et al.

It is certified that error appears in the above-indentified patent and that said Letters Patent is hereby corrected as shown below:

Column 1, line 13: "MF" should read --HF--
          line 51: "WOS910341-A" should read --WO8910341-A--
Column 2, line 12: "$Cr(OH)Cl_2 \cdot 2NH_2O$" should read --$Cr(OH)Cl_2 \cdot 2H_2O$--
          line 42: "$Al_2L_3 \cdot H_2O)$" should read --$Al_2O_3 \cdot H_2O)$--
Column 4, line 44: "beat" should read --beta--
Column 4,    line 46: "$Cr(OH)Cl_2 \cdot 2H_2)$" should read --$Cr(OH)Cl_2 \cdot 2H_2O$--

Signed and Sealed this

Fifteenth Day of November, 1994

Attest:

BRUCE LEHMAN

*Attesting Officer*           *Commissioner of Patents and Trademarks*